United States Patent [19]

Quantock

[11] 4,238,502

[45] Dec. 9, 1980

[54] METHOD OF TREATING PSYCHIATRIC CONDITIONS

[75] Inventor: Derek C. Quantock, Rutland, England

[73] Assignee: Fisons Limited, London, England

[21] Appl. No.: 58,608

[22] Filed: Jul. 18, 1979

[30] Foreign Application Priority Data

Aug. 3, 1978 [GB] United Kingdom ............... 32081/78

[51] Int. Cl.$^3$ .............................................. A61K 31/35
[52] U.S. Cl. .................................................... 424/283
[58] Field of Search ........................................ 424/283

[56] References Cited

U.S. PATENT DOCUMENTS

| | | | |
|---|---|---|---|
| 4,009,280 | 2/1977 | Ross et al. | 424/283 |
| 4,146,634 | 3/1979 | Brown et al. | 424/283 |

*Primary Examiner*—Stanley J. Friedman
*Attorney, Agent, or Firm*—Merriam, Marshall & Bicknell

[57] ABSTRACT

There is described a method for the treatment of psychiatric conditions which method comprises inhalation administration of 1,3-bis(2-carboxychromon-5-yloxy)-2-hydroxy propane, or a pharmaceutically acceptable salt thereof (as active ingredient), to a patient suffering, or liable to suffer, from such a condition.

8 Claims, No Drawings

METHOD OF TREATING PSYCHIATRIC CONDITIONS

This invention relates to a new therapeutic method.

According to the invention there is provided a method of treatment of psychiatric conditions which method comprises inhalation administration of 1,3-bis(2-carboxychromon-5-yloxy)-2-hydroxy propane, or a pharmaceutically acceptable salt thereof, (as active ingredient), to a patient suffering, or liable to suffer, from such a condition.

Suitable pharmaceutically acceptable salts include, for example, ammonium salts, alkali metal salts (e.g. sodium, potassium and lithium), alkaline earth metal salts (e.g. magnesium and calcium), and salts with organic amines (e.g. mono- di- or tri- alkyl C 1 to 6 amines, piperidine, and trialkanol C 1 to 6 amine salts). We prefer to use the disodium salt.

The drug may be administered to mammals, particularly humans and especially children under 10 years of age.

The drug may be administered as a conventional inhalation composition and may be administered through the nose or preferably through the mouth.

In order to produce suitable compositions the drug is worked up with inorganic or organic pharmaceutically acceptable adjuvants or excipients. Examples of such adjuvants are:

For dry powder compositions: Coarse carriers acceptable in the lung, e.g. coarse lactose. Alternatively the pure drug may be formed into soft pellets.

For nebulisation: A solvent e.g. water.

For pressure pack formulations: A compressed gas, e.g. a chloroflurohydrocarbon such as propellant 11, propellant 12, propellant 114 or a mixture of two or more thereof. The compressed gas is preferably used in conjunction with a pharmaceutically acceptable surface active agent, e.g. a sorbitan oleate.

The drug may, if desired, be used in a specific form, e.g. having a substantial number of particles of effective particle size of less than 10 microns or particular crystal habit.

The dosage to be administered will of course vary with the condition to be treated, with its severity and with its location. However in general a dosage of from about 5 to 200, preferably 10 to 160 mg and most preferably 20 to 80 mg of the drug administered 1 to 4 times a day (i.e. a daily dosage of 5 to 800 mg) is found to be satisfactory. The administration preferably takes place before meals.

The administration may, if desired, be carried out at the same time as administration of the active ingredient by swallowing, e.g. in a dosage of from 100 to 1,000 and preferably 200 to 500 mg from 1 to 4 times a day (i.e. a daily dosage of 100 to 4,000 mg). The active ingredient for swallowing may be formulated in conventional form.

Psychiatric conditions which may be treated by the method of the invention include those in which allergy or immune reactions (notably of the GI tract) play a contributory part, and in particular alcoholism, depression, mania, thought disorders, hallucinations, schizophrenia (e.g. caused by gluten sensitivity), manic depression and behavioural problems in children, e.g. hyperactivity.

It is most unusual for inhalation therapy to be used in the treatment of psychiatric conditions and we believe that the present invention provides an unique form of therapy for such conditions.

The invention is illustrated, but in no way limited by the following Example.

EXAMPLE

Eight hyperkinetic children in the age range 6 to 9 were admitted to the trial. All of the children received placebo for one week prior to administration of the drug. Each child was administered orally 600 mg of the disodium salt of 1,3-bis(2-carboxychromon-5-yloxy)-2-hydroxy propane (the drug) daily in the first week, 1200 mg of the drug orally in the second week and up to 2000 mg of the drug orally per week thereafter, the amount of drug administered was where necessary individually adjusted. Each child was also given up to 160 mg per day of the drug by inhalation. Drug therapy was given for 10 weeks to 5 of the children and for 9 and 8 weeks to one child each. One child did not complete the trial.

The following improvements were noted:

(1) hyperactivity marked in four, moderate in one, mild in one, and none in two patients;

(2) sleep disorders marked in four, moderate in one, mild in two, and none in one; and (3) learning problems marked in three, moderate in one, mild in two, and none in two;

Symptoms that improved most were hyperactivity, distractibility and fidgetiness. Improvements were noted in the first three weeks by the parents, teachers and physicians in six patients, and in the fourth week by the teacher and parent in one patient. There was a good agreement on the degree and the onset of improvement between teachers, parents and the physician.

When drug therapy was discontinued, four patients relapsed-three within a few days and one after three weeks. In two cases drug therapy was resumed, resulting in improvement.

I claim:

1. A method of treatment of a psychiatric condition which method comprises administering by inhalation an effective amount of 1,3-bis(2-carboxychromon-5-yloxy)-2-hydroxy propane or a pharmaceutically acceptable salt thereof, as active ingredient, to a patient suffering from such a condition.

2. A method according to claim 1, wherein the active ingredient is the disodium salt of 1,3-bis(2-carboxychromon-5-yloxy)-2-hydroxy propane.

3. A method according to claim 1 wherein the inhalation is through the mouth.

4. A method according to claim 1, wherein from 5 to 200 mg of active ingredient is administered 1 to 4 times a day.

5. A method according to claim 4, wherein from 10 to 160 mg of active ingredient is administered 1 to 4 times a day.

6. A method according to claim 1, wherein the administration is carried out at the same time as administration of the active ingredient by swallowing.

7. A method according to claim 6, wherein the daily swallowed dosage is from 100 to 4000 mg.

8. A method according to claim 1, wherein the condition treated is hyperactivity.

* * * * *